(12) United States Patent
Andree et al.

(10) Patent No.: US 6,228,809 B1
(45) Date of Patent: *May 8, 2001

(54) SUBSTITUTED AMINOPHENYLURACILS AS HERBICIDES AND INSECTICIDES

(75) Inventors: Roland Andree, Landenfeld; Mark Wilhelm Drewes, Langenfeld; Markus Dollinger; Hans-Joachim Santel, both of Leverkusen; Christoph Erdelen, Leichlingen, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/945,768
(22) PCT Filed: Apr. 25, 1996
(86) PCT No.: PCT/EP96/01722
  § 371 Date: Oct. 31, 1997
  § 102(e) Date: Oct. 31, 1997
(87) PCT Pub. No.: WO96/35679
  PCT Pub. Date: Nov. 14, 1996

(30) Foreign Application Priority Data

May 8, 1995 (DE) .............................................. 195 16 785

(51) Int. Cl.$^7$ ........................ C07D 239/45; A01N 43/54
(52) U.S. Cl. ........................ 504/243; 544/310; 544/311; 544/312
(58) Field of Search ............................ 504/243; 544/310, 544/311, 312

(56) References Cited

U.S. PATENT DOCUMENTS

| 5,084,084 | * | 1/1992 | Saton et al. ......................... 544/313 |
| 5,593,945 | * | 1/1997 | Andree et al. ....................... 544/313 |
| 5,759,957 |   | 6/1998 | Andree et al. ....................... 544/311 |

FOREIGN PATENT DOCUMENTS

| 44 37 295 | 10/1995 | (DE) . |
| 0 438 209 | 7/1991  | (EP) . |
| 0 563 384 | 10/1993 | (EP) . |

* cited by examiner

*Primary Examiner*—John M. Ford
(74) *Attorney, Agent, or Firm*—Norris McLaughlin & Marcus

(57) ABSTRACT

The invention relates to novel substituted aminophenyluracils of the general formula (I)

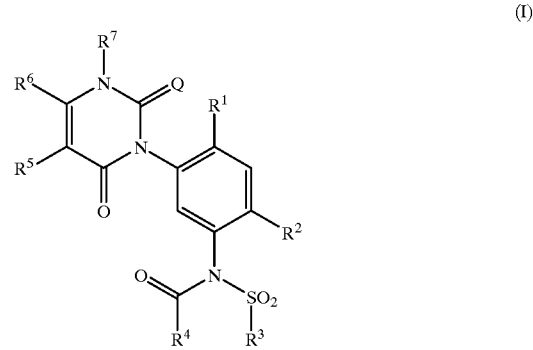

to a process for their preparation and to their use as herbicides and insecticides.

4 Claims, No Drawings

SUBSTITUTED AMINOPHENYLURACILS AS HERBICIDES AND INSECTICIDES

The invention relates to novel substituted aminophenyluracils, to a process for their preparation and to their use as herbicides and insecticides.

It is known that certain substituted aminophenyluracils have herbicidal properties (cf. EP 408382/U.S. Pat. No. 5,084,084/U.S. Pat. No. 5,127,935/U.S. Pat. No. 5,154,755, EP 563384, DE 4412079), but they have hitherto not attained any major importance either as herbicides or as insecticides.

This invention, accordingly, provides the novel substituted aminophenyluracils of the general formula (I)

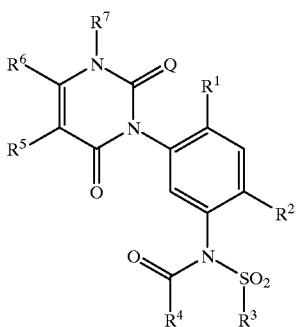

(I)

in which
- Q represents oxygen or sulphur,
- $R^1$ represents hydrogen, cyano or halogen,
- $R^2$ represents cyano, thiocarbamoyl, halogen or represents optionally substituted alkyl,
- $R^3$ represents respectively optionally substituted alkyl, cycloalkyl, aryl, arylalkyl or heteroaryl,
- $R^4$ represents respectively optionally substituted cycloalkyl, aryl or heteroaryl,
- $R^5$ represents hydrogen, halogen or represents respectively optionally substituted alkyl or alkoxy,
- $R^6$ represents optionally substituted alkyl and
- $R^7$ represents hydrogen, hydroxyl, amino or represents respectively optionally substituted alkyl, alkoxy, alkenyl or alkinyl.

The novel substituted aminophenyluracils of the general formula (I) are obtained when appropriate sulphonylaminophenyluracils of the general formula (II)

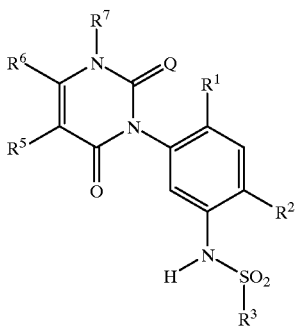

(II)

in which
Q, $R^1$, $R^2$, $R^3$, $R^4$, $R^5$, $R^6$ and $R^7$ are each as defined above, are reacted with acid derivatives of the general formula (III)

$$R^4\text{—CO—X} \quad \text{(III)}$$

in which
- $R^4$ is as defined above and
- X represents halogen or the grouping —O—CO—$R^4$, if appropriate in the presence of a reaction auxiliary and if appropriate in the presence of a diluent.

The novel substituted aminophenyluracils of the general formula (I) have strong herbicidal and insecticidal activity.

In the definitions, the saturated or unsaturated hydrocarbon chains, such as alkyl, alkenyl or alkinyl, are in each case straight-chain or branched.

Halogen generally represents fluorine, chlorine, bromine or iodine, preferably fluorine, chlorine or bromine, in particular fluorine or chlorine.

The invention preferably provides compounds of the formula (I) in which
- Q represents oxygen or sulphur,
- $R^1$ represents hydrogen, cyano, fluorine or chlorine,
- $R^2$ represents cyano, thiocarbamoyl, fluorine, chlorine, bromine, or represents optionally fluorine- and/or chlorine-substituted alkyl having 1 to 4 carbon atoms,
- $R^3$ represents optionally cyano-, fluorine-, chlorine-, bromine-, $C_1$–$C_4$-alkoxy- or $C_1$–$C_4$-alkylthio-substituted alkyl having 1 to 6 carbon atoms,
- $R^3$ furthermore represents optionally cyano-, fluorine-, chlorine-, bromine- or $C_1$–$C_4$-alkyl-substituted cycloalkyl having 3 to 8 carbon atoms,
- $R^3$ furthermore represents phenyl, naphthyl, benzyl, phenylethyl, thienyl, pyrazolyl, pyridinyl or quinolinyl, possible substituents in each case being:
    fluorine, chlorine, bromine, cyano, nitro, carboxy, carbamoyl, thiocarbamoyl, $C_1$–$C_4$-alkyl, $C_1$–$C_4$-alkoxy, $C_1$–$C_4$-alkylthio, dimethylaminosulphonyl, diethylaminosulphonyl, respectively optionally fluorine- and/or chlorine-substituted $C_1$–$C_4$-alkylsulphinyl or $C_1$–$C_4$-alkylsulphonyl, respectively optionally fluorine-, chlorine-, bromine-, cyano-, methoxy- or ethoxy-substituted $C_1$–$C_4$-alkoxycarbonyl or respectively optionally fluorine-, chlorine-, bromine-, cyano-, methyl-, methoxy-, trifluoromethyl- and/or trifluoromethoxy-substituted phenyl, phenyloxy or phenylthio;
- $R^4$ represents optionally cyano-, fluorine-, chlorine-, bromine- or $C_1$–$C_4$-alkyl-substituted cycloalkyl having 3 to 8 carbon atoms,
- $R^4$ furthermore represents respectively optionally substituted phenyl, naphthyl, furyl, thienyl, oxazolyl, isoxazolyl, pyrazolyl, pyridinyl, pyrimidinyl or quinolinyl, possible substituents in each case being:
    fluorine, chlorine, bromine, cyano, nitro, carboxy, carbamoyl, thiocarbamoyl, dimethylamino, dinethylaminosulphonyl, diethylaminosulphonyl, respectively optionally fluorine- and/or chlorine-substituted $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl or optionally fluorine-, chlorine-, bromine-, cyano-, methoxy- or ethoxy-substituted $C_1$–$C_4$-alkoxycarbonyl;
- $R^5$ represents hydrogen, fluorine, chlorine, bromine or represents respectively optionally fluorine- and/or chlorine-substituted alkyl or alkoxy having in each case 1 to 4 carbon atoms, $R^6$ represents optionally fluorine- and/or chlorine-substituted alkyl having 1 to 4 carbon atoms and $R^7$ represents hydrogen, hydroxyl, amino or represents respectively optionally fluorine-, chlorine- or $C_1$–$C_4$-alkoxy-substituted alkyl, alkoxy, alkenyl or alkinyl having in each case up to 6 carbon atoms.

The invention in particular provides compounds of the formula (I) in which

Q represents oxygen or sulphur, $R^1$ represents hydrogen, cyano, fluorine or chlorine, $R^2$ represents cyano, thiocarbamoyl, fluorine, chlorine, bromine, methyl, ethyl, n- or i-propyl, n-, i-, s- or t-butyl or trifluoromethyl, $R^3$ represents respectively optionally cyano-, fluorine-, chlorine-, methoxy- or ethoxy-substituted methyl, ethyl, n- or i-propyl, n-, i-, s- or t-butyl, $R^3$ furthermore represents respectively optionally cyano-, fluorine-, chlorine-, bromine-, methyl-, ethyl-, n- or i-propyl-substituted cyclopropyl, cyclobutyl, cyclopentyl or cyclohexyl, $R^3$ furthermore represents respectively optionally substituted phenyl, naphthyl, benzyl, phenylethyl, thienyl, pyrazolyl, pyridinyl or quinolinyl, possible substituents being: fluorine, chlorine, bromine, cyano, nitro, carboxy, carbamoyl, thiocarbamoyl, methyl, ethyl, n- or i-propyl, trifluoromethyl, methoxy, ethoxy, n- or i-propoxy, difluoromethoxy, trifluoromethoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, dimethylaminosulphonyl, diethylaminosulphonyl, methoxycarbonyl, ethoxycarbonyl, n- or i-propoxycarbonyl, $R^4$ represents optionally cyano-, fluorine-, chlorine-, bromine-, methyl-, ethyl-, n- or i-propyl-substituted cyclopropyl, cyclobutyl, cyclopentyl or cyclohexyl, $R^4$ furthermore represents respectively optionally substituted phenyl, naphthyl, furyl, thienyl, oxazolyl, isoxazolyl, pyrazolyl, pyridinyl or pyrimidinyl, possible substituents in each case being: fluorine, chlorine, bromine, cyano, nitro, carboxy, carbamoyl, thiocarbamoyl, dimethylamino, dimethylaminosulphonyl or diethylaminosulphonyl, respectively optionally fluorine- and/or chlorine-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, respectively optionally fluorine-, chlorine-, bromine-, cyano-, methoxy- or ethoxy-substituted methoxycarbonyl, ethoxycarbonyl, n- or i-propoxycarbonyl, respectively optionally fluorine-, chlorine-, bromine-, cyano-, methyl-, methoxy-, trifluoromethyl- and/or trifluoromethoxy-substituted phenyl, phenyloxy or phenylthio, $R^5$ represents hydrogen, fluorine, chlorine, bromine or represents respectively optionally fluorine- and/or chlorine-substituted methyl, ethyl, n- or i-propyl, $R^6$ represents optionally fluorine- and/or chlorine-substituted methyl, ethyl, n- or i-propyl and $R^7$ represents hydrogen, amino or represents respectively optionally fluorine- and/or chlorine-substituted methyl, ethyl, n- or i-propyl, n-, i- or s-butyl, methoxy, ethoxy, n- or i-propoxy, n-, i- or s-butoxy, propenyl, butenyl, propinyl or butinyl.

The general or preferred radical definitions listed above are valid radicals for the end products of formula (I) and also, in a corresponding manner, for the starting materials or intermediates which are required in each case for the preparation. These radical definitions can be combined with each other at will, i.e. combinations between the given preferred ranges are also possible.

Using, for example, 1-(4-chloro-2-fluoro-5-methylsulphonylamino-phenyl)-3,6-dihydro-2,6-dioxo-3,4-dimethyl-1(2H)-pyrimidine and 2-fluoro-benzoyl chloride as starting materials, the course of the reaction in the process according to the invention can be illustrated by the following scheme:

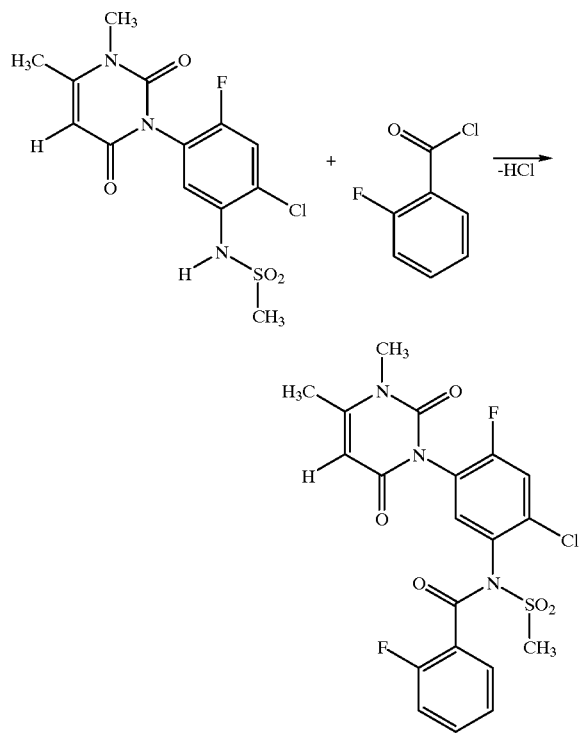

The formula (II) provides a general definition of the sulphonylaminophenyl-uracils to be used as starting materials in the process according to the invention for preparing the compounds of the formula (I). In the formula (II), Q, $R^1$, $R^2$, $R^3$, $R^5$, $R^6$ and $R^7$ each preferably or in particular have those meanings which have already been indicated above, in connection with the description of the compounds of the formula (I) to be prepared according to the invention, as being preferred or particularly preferred for Q, $R^1$, $R^2$, $R^3$, $R^5$, $R^6$ and $R^7$.

The starting materials of the formula (II) are known and/or can be prepared by processes known per se (cf. EP 408382/U.S. Pat. No. 5,084,084/U.S. Pat. No. 5,127,935/U.S. Pat. No. 5,154,755, EP 563384, DE 4412079).

The formula (III) provides a general definition of the acyl halides further to be used as starting materials in the process according to the invention for preparing the compounds of the formula (I). In the formula (III), $R^4$ preferably or in particular has that meaning which has already been indicated above, in connection with the description of the compounds of the formula (I) to be prepared according to the invention, as being preferred or particularly preferred for $R^4$; X preferably represents fluorine, chlorine or bromine, in particular chlorine.

The starting materials of the formula (III) are known chemicals for synthesis.

The process according to the invention for preparing the compounds of the formula (I) is preferably carried out in the presence of a suitable reaction auxiliary. Suitable reaction auxiliaries are generally the customary inorganic or organic bases or acid acceptors. These include preferably alkali metal or alkaline earth metal acetates, amides, carbonates, bicarbonates, hydrides, hydroxides or alkoxides such as, for example, sodium acetate, potassium acetate or calcium acetate, lithium amide, sodium amide, potassium amide or calcium amide, sodium carbonate, potassium carbonate or. calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide; furthermore also basic organic nitrogen compounds such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N methyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo [4.3.0]-non-5-ene (DBN), or 1,8-diazabicyclo[5.4.0]-undec-7-ene (DBU).

The process according to the invention for preparing the compounds of the formula (I) is preferably carried out in the presence of a diluent. Suitable diluents are generally the customary organic solvents. These preferably include aliphatic, alicyclic and aromatic, optionally halogenated hydrocarbons such as, for example, pentane, hexane, heptane, petroleum ether, ligroin, benzine, benzene, toluene, xylene, chlorobenzene, dichlorobenzene, cyclohexane, methylcyclohexane, dichloromethane (methylene chloride), trichloromethane (chloroform) or tetrachloromethane, dialkyl ethers such as, for example, diethyl ether, diisopropyl ether, methyl t-butyl ether, ethyl t-butyl ether, methyl t-pentyl ether (MTBE), ethyl t-pentyl ether, tetrahydrofuran (THF), 1,4-dioxane, ethylene glycol dimethyl ether or ethylene glycol diethyl ether, diethylene glycol dimethyl ether or diethylene glycol diethyl ether; dialkyl ketones, such as, for example, acetone, butanone (methyl ethyl ketone), methyl i-propyl ketone or methyl i-butyl ketone, nitriles such as, for example, acetonitrile, propionitrile, butyronitrile or benzonitrile; amides such as, for example, N,N-dimethyl-formamide (DMF), N,N-dimethyl-acetamide, N-methyl-formamide, N-methyl-pyrrolidone or hexamethyl-phosphoric triamide; esters such as, for example, methyl acetate, ethyl acetate, n- or i-propyl acetate, n-, i- or s-butyl acetate; sulphoxides such as, for example, dimethyl sulphoxide; alkanols such as, for example, methanol, ethanol, n- or i-propanol, n-, i-, s- or t-butanol, ethylene glycol monomethyl ether or ethylene glycol monoethyl ether, diethylene glycol monomethyl ether or diethylene glycol monoethyl ether, mixtures thereof with water or pure water.

When carrying out the process according to the invention, the reaction temperatures can be varied over a relatively wide range. In general, temperatures of between −10° C. and +150° C., preferably temperatures of between 0° C. and 100° C., are employed.

The process according to the invention is generally carried out under atmospheric pressure ("normal pressure"). However, it is also possible to operate under elevated or reduced pressure—in general between 0.1 bar and 10 bar.

In the practice of the process according to the invention, the starting materials are generally employed in approximately equimolar amounts. However, it is also possible to use one of the components in a relatively large excess. The reaction is generally carried out in a suitable diluent in the presence of a reaction auxiliary, and the reaction mixture is generally stirred for several hours at the temperature required. Work-up is carried out according to customary methods (cf. the Preparation Examples).

The active compounds according to the invention can be used as defoliants, desiccants, haul-killers and, especially, as weed-killers. By weeds, in the broadest sense, are to be understood all plants which grow in locations where they are undesired. Whether the substances according to the invention act as total or selective herbicides depends essentially on the amount used.

The active compounds according to the invention can be used, for example, in connection with the following plants:

Dicotyledonous Weeds of the Genera:

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus and Taraxacum.

Dicotyledonous Crops of the Genera:

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous Weeds of the Genera:

Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous Crops of the Genera:

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds of the formula (I) are suitable, depending on the concentration, for the total control of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The compounds of the formula (I) according to the invention are particularly suitable for the selective control of monocotyledonous and dicotyledonous weeds in monocotyledonous crops pre- and post-emergence.

The active compounds are suitable for controlling animal pests, preferably arthropods and nematodes, in particular insects and arachnids, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Macrosiphum avenae*, Myzus spp., Pemphigus spp., *Phorodon humuli, Phylloxera vastatrix, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fiumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit, Phorbia spp., Pegomyia hyoscyami, Ceratitis capitata, Dacus oleae* and *Tipula paludosa*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include, for example, Pratylenchus spp., Radopholus spp., Ditylenchus spp., Tylenchulus spp., Heterodera spp., Globodera spp., Meloidogyne spp., Aphelenchoides spp., Longidorus spp., Xiphinema spp., Trichodorus spp., Tylenchus spp., Helicotylenchus spp., Rotylenchus spp. and Tylenchulus spp.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water.

As solid carriers there are suitable:
for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural Tocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be used as such or, in their formulations, as a mixture with known herbicides for the control of weeds, in which case ready-to-use formulations or tank mixes are possible.

Suitable co-components for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr, aryloxyphenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulfonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, diallate, EPTC, esprocarb, molinate, prosulfocarb, thiobencarb and triallate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha The preparation and the use of the active compounds according to the invention can be seen from the examples below.

PREPARATION EXAMPLES

Exmple 1

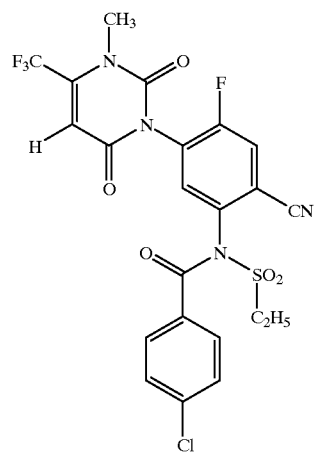

At about 20° C., 0.90 g (5 mmol) of 4-chloro-benzoyl chloride are added to a mixture of 2.1 g (5 mmol) of 1-(4cyano-5-ethylsulphonylamino-2-fluoro-phenyl)-3,6-dihydro-2,6-dioxo-3-methyl-4-trifluoromethyl-1(2H)-pyrimidine, 0.60 g (6 mmol) of triethylamine and 50 ml of acetonitrile, and the reaction mixture is stirred at 20° C. for 2 hours. The mixture is then concentrated using waterpump vacuum and the residue is taken up in chloroform, washed with 2N hydrochloric acid, dried with sodium sulphate and filtered. The filtrate is concentrated using waterpump vacuum, the residue is digested with diethyl ether and the resulting crystalline product is isolated by filtration with suction.

1.5 g (54% of theory) of 1-[4-cyano-5-(N-ethylsulphonyl-N-(4-chlorobenzoyl)amino)2-fluoro-phenyl]-3,6-dihydro-2,6-dioxo-3-methyl-4-trifluoromethyl-1(2H)-pyrimidine of melting point 138° C. are obtained.

Example 2

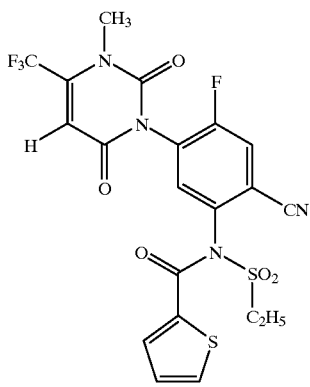

At about 20° C., 1.8 g (12 mmol) of thiophene-2-carbonyl chloride are added to a mixture of 2.1 g (5 mmol) of 1-(4-cyano-5-ethylsulphonylamino-2-fluoro-phenyl)-3,6-dihydro-2,6-dioxo-3-methyl-4-trifluoromethyl-1(2H)-pyrimidine, 1.5 ml of pyridine and 50 ml of methylene chloride, and the reaction mixture is stirred at 20° C. for one week. The solution is then washed with 1N hydrochloric acid, dried with sodium sulphate and filtered. The filtrate is concentrated using using waterpump vacuum, the residue is digested with diethyl ether and the resulting crystalline product is isolated by filtration with suction.

2.1 g (84% of theory) of 1-[4-cyano-5-(N-ethylsulphonyl-N-(thien-2-yl-carbonyl)amino)-2-fluoro-phenyl]-3,6-dihydro-2,6-dioxo-3-methyl-4-trifluoromethyl-1(2H)-pyrimidine of melting point 192° C. are obtained.

By proceeding similarly to Examples 1 and 2 and according to the general description of the preparative process of the invention, it is also possible to prepare, for example, the compounds of the formula (I) listed below in Table 1.

TABLE 1

Examples of compounds of the formula (I)

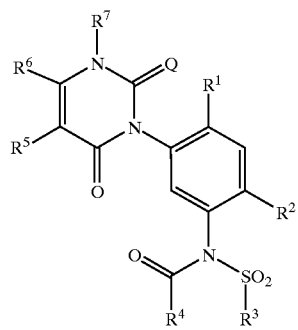

(I)

| Ex. No. | Q | $R^1$ | $R^2$ | $R^3$ | $R^4$ | $R^5$ | $R^6$ | $R^7$ | Melting point (° C.) |
|---|---|---|---|---|---|---|---|---|---|
| 3 | O | F | CN | $C_2H_5$ |  | H | $CF_3$ | $CH_3$ | 93 |
| 4 | O | F | CN | $C_2H_5$ | 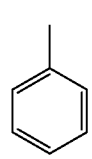 | H | $CF_3$ | $CH_3$ | 108 |
| 5 | O | F | CN | $C_2H_5$ | 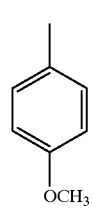 | H | $CF_3$ | $CH_3$ | 157 |
| 6 | O | F | CN | $C_2H_5$ | 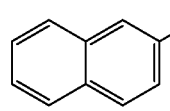 | H | $CF_3$ | $CH_3$ | 190 |

TABLE 1-continued
Examples of compounds of the formula (I)
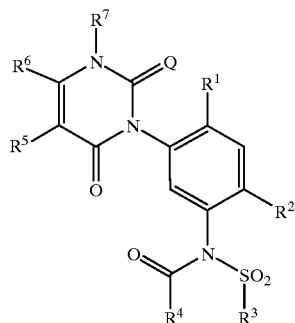
(I)
| Ex. No. | Q | $R^1$ | $R^2$ | $R^3$ | $R^4$ | $R^5$ | $R^6$ | $R^7$ | Melting point (° C.) |
|---|---|---|---|---|---|---|---|---|---|
| 7 | O | F | CN | $C_2H_5$ | 1-naphthyl | H | $CF_3$ | $CH_3$ | 186 |
| 8 | O | F | CN | $C_2H_5$ | 3,4-dichlorophenyl | H | $CF_3$ | $CH_3$ | 206 |
| 9 | O | F | CN | $C_2H_5$ | 2,4-difluorophenyl | H | $CF_3$ | $CH_3$ | 123 |
| 10 | O | F | CN | $C_2H_5$ | 4-methylphenyl | H | $CF_3$ | $CH_3$ | 191 |
| 11 | O | F | CN | $CH_3$ | 4-chlorophenyl | H | $CF_3$ | $CH_3$ | 215 |
| 12 | O | F | CN | $CH_3$ | 2-chlorophenyl | H | $CF_3$ | $CH_3$ | 189 |

TABLE 1-continued

Examples of compounds of the formula (I)

(I)

| Ex. No. | Q | R¹ | R² | R³ | R⁴ | R⁵ | R⁶ | R⁷ | Melting point (° C.) |
|---|---|---|---|---|---|---|---|---|---|
| 13 | O | F | CN | $CH_3$ | 3-chlorophenyl | H | $CF_3$ | $CH_3$ | 189 |
| 14 | O | F | CN | $CH_3$ | 2-fluorophenyl | H | $CF_3$ | $CH_3$ | 201 |
| 15 | O | F | CN | $CH_3$ | 3-fluorophenyl | H | $CF_3$ | $CH_3$ | 175 |
| 16 | O | F | CN | $CH_3$ | 2-bromophenyl | H | $CF_3$ | $CH_3$ | 184 |
| 17 | O | F | CN | $CH_3$ | phenyl | H | $CF_3$ | $CH_3$ | 193 |
| 18 | O | F | CN | $CH_3$ | 2-thienyl | H | $CF_3$ | $CH_3$ | 203 |
| 19 | O | F | CN | $CH_3$ | 3-methyl-2-thienyl | H | $CF_3$ | $CH_3$ | 202 |

TABLE 1-continued
Examples of compounds of the formula (I)
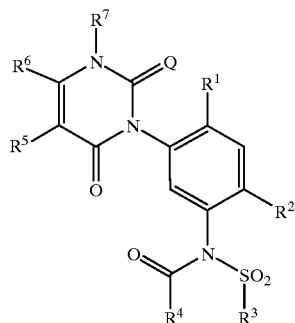
(I)
| Ex. No. | Q | R¹ | R² | R³ | R⁴ | R⁵ | R⁶ | R⁷ | Melting point (° C.) |
|---|---|---|---|---|---|---|---|---|---|
| 20 | O | H | CN | CH₃ | 4-Cl-C₆H₄ | H | CF₃ | CH₃ | |
| 21 | O | Cl | Cl | CH₃ | 4-Cl-C₆H₄ | H | CF₃ | CH₃ | |
| 22 | O | H | CN | C₂H₅ | 4-Cl-C₆H₄ | H | CF₃ | CH₃ | |
| 23 | O | F | CN | n-C₃H₇ | 4-Cl-C₆H₄ | H | CF₃ | CH₃ | |
| 24 | O | F | CN | n-C₄H₉ | 2-F-C₆H₄ | H | CF₃ | CH₃ | |
| 25 | O | F | CN | CH₃ | 2-F-C₆H₄ | H | CF₃ | C₂H₅ | |

TABLE 1-continued
Examples of compounds of the formula (I)
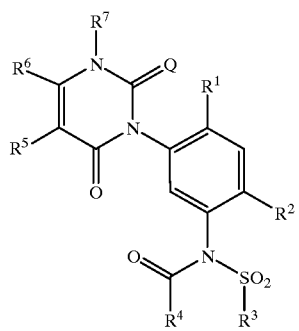
(I)
| Ex. No. | Q | $R^1$ | $R^2$ | $R^3$ | $R^4$ | $R^5$ | $R^6$ | $R^7$ | Melting point (° C.) |
|---|---|---|---|---|---|---|---|---|---|
| 26 | O | Cl | CN | $CH_3$ | 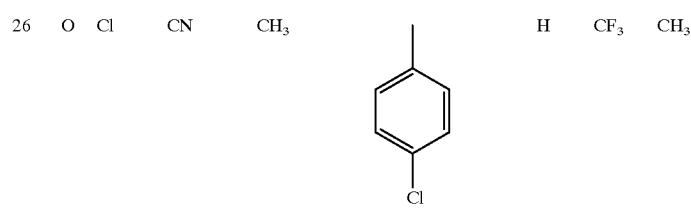 | H | $CF_3$ | $CH_3$ | |
| 27 | O | Cl | CN | $CH_3$ | 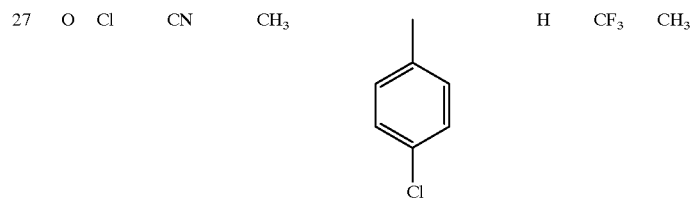 | H | $CF_3$ | $CH_3$ | |
| 28 | O | Cl | CN | $n\text{-}C_3H_7$ | 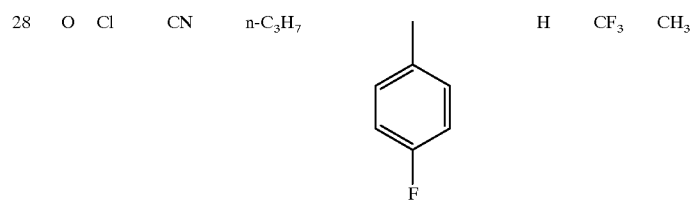 | H | $CF_3$ | $CH_3$ | |
| 29 | O | F | CN | $i\text{-}C_3H_7$ | 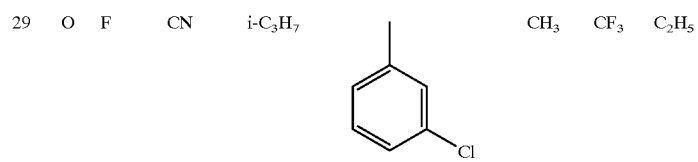 | $CH_3$ | $CF_3$ | $C_2H_5$ | |
| 30 | O | F | CN | 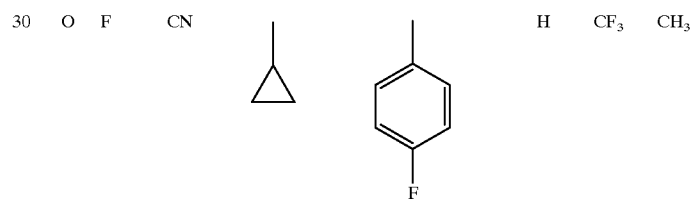 | | H | $CF_3$ | $CH_3$ | |

TABLE 1-continued
Examples of compounds of the formula (I)
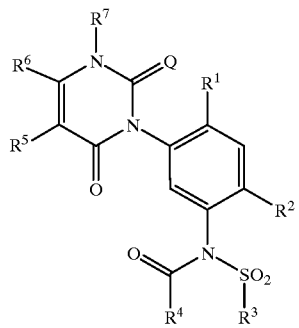
(I)
| Ex. No. | Q | R¹ | R² | R³ | R⁴ | R⁵ | R⁶ | R⁷ | Melting point (° C.) |
|---|---|---|---|---|---|---|---|---|---|
| 31 | O | F | CN | n-C₄H₉ | 4-CF₃-C₆H₄ | H | CF₃ | NH₂ | |
| 32 | O | F | CN | i-C₄H₉ | 4-NO₂-C₆H₄ | H | CF₂Cl | CH₃ | |
| 33 | O | Cl | C(S)NH₂ | CH₃ | 3-OCH₃-C₆H₄ | H | CF₃ | CH₃ | |
| 34 | O | F | C(S)NH₂ | CH₃ | 4-CN-C₆H₄ | H | C₂F₅ | CH₃ | |
| 35 | O | F | CN | CH₃ | 4-CN-C₆H₄ | H | CF₃ | CH₃ | |

TABLE 1-continued
Examples of compounds of the formula (I)
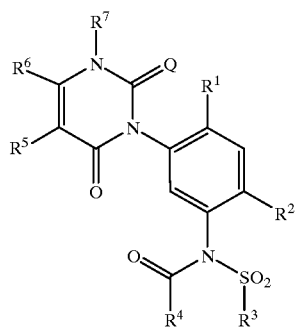
(I)
| Ex. No. | Q | $R^1$ | $R^2$ | $R^3$ | $R^4$ | $R^5$ | $R^6$ | $R^7$ | Melting point (° C.) |
|---|---|---|---|---|---|---|---|---|---|
| 36 | O | F | CN | $CH_3$ | 4-CN-C$_6$H$_4$ | H | $CHF_2$ | $CH_3$ | |
| 37 | O | F | CN | $C_2H_5$ | 4-CN-C$_6$H$_4$ | H | $CF_3$ | $CH_3$ | |
| 38 | O | F | CN | $CH_3$ | 4-OCF$_3$-C$_6$H$_4$ | H | $CF_3$ | $CH_3$ | |
| 39 | O | F | CN | $CH_3$ | 2-OCF$_3$-C$_6$H$_4$ | H | $CF_3$ | $CH_3$ | |
| 40 | O | F | CN | $CH_3$ | 2-COOCH$_3$-C$_6$H$_4$ | H | $CF_3$ | $CH_3$ | |
| 41 | O | F | CN | $C_2H_5$ | 4-COOC$_2$H$_5$-C$_6$H$_4$ | H | $CHF_2$ | $CH_3$ | |

TABLE 1-continued
Examples of compounds of the formula (I)
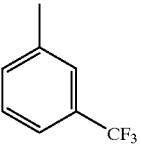
| Ex. No. | Q | R$^1$ | R$^2$ | R$^3$ | R$^4$ | R$^5$ | R$^6$ | R$^7$ | Melting point (° C.) |
|---|---|---|---|---|---|---|---|---|---|
| 42 | O | F | CN | C$_2$H$_5$ | 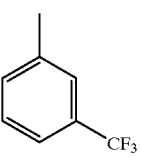 | H | CF$_3$ | CH$_3$ | |
| 43 | O | F | CN | CH$_3$ | 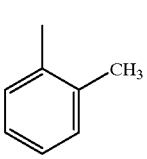 | H | CF$_3$ | CH$_3$ | |
| 44 | O | F | CN | CH$_3$ | 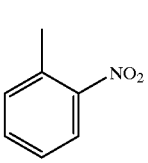 | H | CF$_3$ | CH$_3$ | |
| 45 | O | F | CN | CH$_3$ | 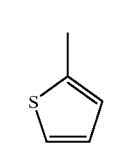 | H | CF$_3$ | CH$_3$ | |
| 46 | O | F | CN | CH$_3$ | 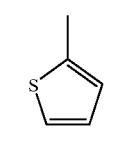 | H | CF$_3$ | NH$_2$ | 268 |
| 47 | S | F | CN | C$_2$H$_5$ | 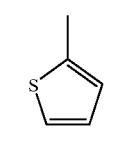 | CH$_3$ | CF$_3$ | CH$_3$ | |
| 48 | O | F | CN | n-C$_3$H$_7$ | 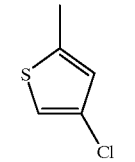 | H | CF$_3$ | CH$_3$ | |

TABLE 1-continued

Examples of compounds of the formula (I)

| Ex. No. | Q | R¹ | R² | R³ | R⁴ | R⁵ | R⁶ | R⁷ | Melting point (° C.) |
|---|---|---|---|---|---|---|---|---|---|
| 49 | O | F | CN | CH₃ | 3-pyridyl (3-methyl) | H | CF₃ | CH₃ | |
| 50 | O | F | CN | CH₃ | 5-methyl-2-chloropyridin-yl | H | CF₃ | CH₃ | |
| 51 | S | F | CN | CH₃ | 4-pyridyl (4-methyl) | H | CF₃ | CH₃ | |
| 52 | S | F | CN | CH₃ | 2,3-dimethylphenyl | H | CF₃ | CH₃ | |
| 53 | S | F | CN | CH₃ | 4-cyanophenyl (methyl) | H | CF₃ | CH₃ | |
| 54 | S | F | CN | CH₃ | 4-fluorophenyl | H | CF₃ | CH₃ | |

TABLE 1-continued

Examples of compounds of the formula (I)

| Ex. No. | Q | $R^1$ | $R^2$ | $R^3$ | $R^4$ | $R^5$ | $R^6$ | $R^7$ | Melting point (° C.) |
|---|---|---|---|---|---|---|---|---|---|
| 55 | S | F | CN | $CH_3$ | phenyl | H | $CF_3$ | $CH_3$ | |
| 56 | O | F | CN | $CH_3$ | 2,6-difluorophenyl | H | $CF_3$ | $CH_3$ | |
| 57 | O | F | CN | $CH_3$ | 2-chloro-6-fluorophenyl | H | $CF_3$ | $CH_3$ | |
| 58 | O | F | CN | $CH_3$ | 2,6-dichlorophenyl | H | $CF_3$ | $CH_3$ | |
| 59 | O | F | CN | $C_2H_5$ | cyclobutyl | H | $CF_3$ | $CH_3$ | 173 |
| 60 | O | F | CN | $C_2H_5$ | cyclopentyl | H | $CF_3$ | $CH_3$ | 192 |
| 61 | O | F | CN | $C_2H_5$ | cyclohexyl | H | $CF_3$ | $CH_3$ | 188 |

TABLE 1-continued
Examples of compounds of the formula (I)
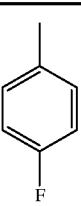
(I)
| Ex. No. | Q | R¹ | R² | R³ | R⁴ | R⁵ | R⁶ | R⁷ | Melting point (° C.) |
|---|---|---|---|---|---|---|---|---|---|
| 62 | O | F | CN | $C_2H_5$ | 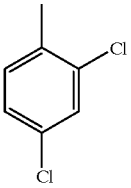 | H | $CF_3$ | $CH_3$ | 188 |
| 63 | O | F | CN | $C_2H_5$ | 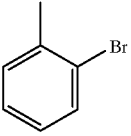 | H | $CF_3$ | $CH_3$ | 122 |
| 64 | O | F | CN | $C_2H_5$ | 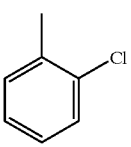 | H | $CF_3$ | $CH_3$ | 164 |
| 65 | O | F | CN | $C_2H_5$ | 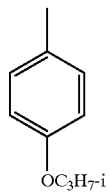 | H | $CF_3$ | $CH_3$ | 159 |
| 66 | O | F | CN | $C_2H_5$ | 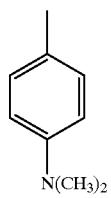 | H | $CF_3$ | $CH_3$ | 107 |
| 67 | O | F | CN | $C_2H_5$ |  | H | $CF_3$ | $CH_3$ | 198 |

TABLE 1-continued

Examples of compounds of the formula (I)

(I)

| Ex. No. | Q | R¹ | R² | R³ | R⁴ | R⁵ | R⁶ | R⁷ | Melting point (° C.) |
|---|---|---|---|---|---|---|---|---|---|
| 68 | O | F | CN | $C_2H_5$ | 2-thienyl | H | $CF_3$ | H | 187 |
| 69 | O | F | CN | $C_2H_5$ | 2-thienyl | H | $CF_3$ | $NH_2$ | 120 |
| 70 | O | F | CN | $CH_3$ | 4-methylphenyl | H | $CF_3$ | $CH_3$ | 227 |
| 71 | O | F | CN | $CH_3$ | 3,4,5-trimethylisoxazol-4-yl | H | $CF_3$ | $CH_3$ | 241 |
| 72 | O | F | CN | $CH_3$ | cyclobutyl | H | $CF_3$ | $CH_3$ | 219 |
| 73 | O | F | CN | $CH_3$ | cyclopentyl | H | $CF_3$ | $CH_3$ | 199 |
| 74 | O | F | CN | $CH_3$ | cyclohexyl | H | $CF_3$ | $CH_3$ | 178 |

TABLE 1-continued
Examples of compounds of the formula (I)
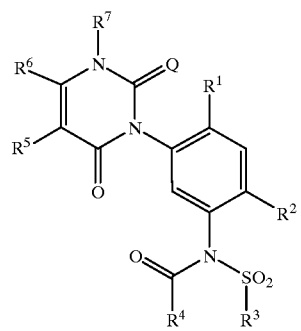
(I)
| Ex. No. | Q | R¹ | R² | R³ | R⁴ | R⁵ | R⁶ | R⁷ | Melting point (° C.) |
|---|---|---|---|---|---|---|---|---|---|
| 75 | O | F | CN | CH₃ | -C₆H₄-OCH₃ (p) | H | CF₃ | CH₃ | 222 |
| 76 | O | F | CN | CH₃ | -C₆H₄-COOCH₃ (p) | H | CF₃ | CH₃ | 225 |
| 77 | O | F | CN | CH₃ | -C₆H₄-OCH(CH₃)₂ (p) | H | CF₃ | CH₃ | 195 |
| 78 | O | F | CN | CH₃ | -C₆H₄-N(CH₃)₂ (p) | H | CF₃ | CH₃ | 216 |
| 79 | O | F | CN | C₂H₅ | cyclopropyl | H | CF₃ | NH₂ | 89 |
| 80 | O | F | CN | C₂H₅ | cyclobutyl | H | CF₃ | NH₂ | 105 |
| 81 | O | F | CN | C₂H₅ | cyclopentyl | H | CF₃ | NH₂ | >200 |

Use Examples

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered or sprayed with the preparation of the active compound. It is advantageous to keep the amount of water per unit area constant. The concentration of the active compound in the preparation is immaterial, only the amount of active compound applied per unit area matters. After three weeks, the degree of damage to the plants is rated in % damage by comparison with the development of the untreated control.

The figures denote:

0%=no effect (like untreated control)

100%=total destruction

In this test, very strong activity against weeds such as cyperus (60–100%), lolium (70–90%), panicum (70–95%), abutilon (100%), chenopodium (100%) and datura (100%) is shown, for example, by the compounds of Preparation Examples 1 and 2 at an application rate of 60 g/ha, combined with very good tolerance by crops such as, for example, maize (0%).

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular mixed amounts of active compound are applied in 1000 l/ha After three weeks, the degree of damage to the plants is rated in % damage by comparison with the development of the untreated control.

The figures denote:

0%=no effect (like untreated control)

100%=total destruction

In this test, very strong activity against weeds such as echinochloa (95%), sorghum (70–80%), abutilon (100%), chenopodium (100%), datura (100%) and solanum (100%) is shown, for example, by the compounds of Preparation Examples 1 and 2 at an application rate of 30 g/ha, combined with good tolerance by crops such as, for example, barley (0–10%).

Example C

Phaedon Larvae Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the desired period of time, the destruction in % is determined. 100% means that all the beetle larvae have been killed; 0% means that none of the beetle larvae have been killed.

In this test, a destruction of 80 to 100% was caused, after 7 days, for example by the compounds of Preparation Examples 1 and 2 at an active compound concentration of 0.1%.

Example D

Nephotettix Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of the active compound of the desired concentration and are infested with larvae of the green rice leafhopper (*Nephotettix cincticeps*) while the seedlings are still moist After the desired period of time, the destruction in % is determined. 100% means that all the leafhoppers have been killed; 0% means that none of the leafhoppers have been killed.

In this test, a destruction of 100% was caused, after 6 days, for example by the compounds of Preparation Examples 1 and 2 at an active compound concentration of 0.1%.

What is claimed is:

1. A compound of formula (I)

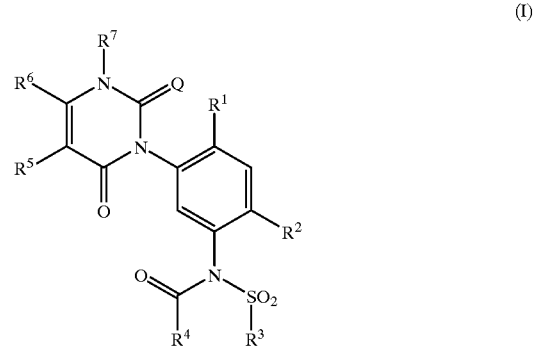

(I)

wherein

Q is oxygen or sulphur;

$R^1$ is hydrogen, cyano, fluorine, or chlorine;

$R^2$ is cyano;

$R^3$ is an optionally substituted alkyl having 1 to 6 carbon atoms, wherein the substituents are cyano-, fluorine-, chlorine-, bromine-, $C_1$–$C_4$-alkoxy-, or $C_1$–$C_4$-alkylthio-, $R^3$ is an optionally substituted cycloaLkyl having 3 to 8 carbon atoms, wherein the substituents are cyano-, fluorine-, chlorine-, bromine-, or $C_1$–$C_4$-alkyl-, $R^3$ is an optionally substituted phenyl, naphthyl, benzyl, phenylethyl, thienyl, pyrazolyl, pyridinyl, or quinolinyl, wherein the substituents are:
  fluorine, chlorine, bromine, cyano, nitro, carboxy, carbamoyl, thiocarbamoyl, $C_1$–$C_4$-alkyl, $C_1$–$C_4$-alkoxy, $C_1$–$C_4$-alkyltio, dimethylaminosulphonyl, or diethylaminosulphonyl,
  optionally substituted $C_1$–$C_4$-alkylsulphinyl or $C_1$–$C_4$-alkylsulphonyl, wherein the substituents are fluorine- or chlorine-,
  optionally substituted $C_1$–$C_4$-alkoxycarbonyl, wherein the substituents are fluorine-, chlorine-, bromine-, cyano-, methoxy-, or ethoxy-,
  optionally substituted phenyl, phenyloxy, or phenylthio, wherein the substituents are fluorine-, chlorine-, bromine-, cyano-, methyl-, methoxy-, trifluoromethyl-, or trifluoromethoxy-;

$R^4$ is an optionally substituted cycloalkyl having 5 to 8 carbon atoms, wherein the substituents are cyano-, fluorine-, chlorine-, bromine-, or $C_1$–$C_4$-alkyl-, $R^4$ is an optionally substituted naphthyl, furyl, thienyl, oxazolyl, isoxazolyl, pyrazolyl, pyridinyl, pyrimidinyl, or quinolinyl, wherein the substituents are:
  fluorine, chlorine, bromine, cyano, nitro, carboxy, carbamoyl, thiocarbamoyl, dimethylamino, dimethylaminosulphonyl, or diethylaminosulphonyl,
  optionally substituted $C_1$–$C_4$-alkyl, $C_1$–$C_4$-alkoxy, $C_1$–$C_4$-alkylthio, $C_1$–$C_4$-alkylsulphinyl, or $C_1$–$C_4$-alkylsulphonyl, wherein the substituents are fluorine- or chlorine-,
  optionally substituted $C_1$–$C_4$-alkoxycarbonyl, wherein the substituents are fluorine-, chlorine-, bromine-, cyano-, methoxy- or ethoxy-;

$R^5$ is hydrogen, fluorine, chlorine, bromine, or is an optionally substituted alkyl or alkoxy having, in each case, 1 to 4 carbon atoms, wherein the substituents are fluorine- or chlorine-;

$R^6$ is an optionally substituted alkyl having 1 to 4 carbon atoms, wherein the substituents are fluorine- or chlorine-; and $R^7$ is hydrogen, hydroxyl, amino, or optionally substituted alkyl, alkoxy, alkenyl, or alkinyl having, in each case, 1 through 6 carbon atoms, wherein the substituents are fluorine, chlorine, or $C_1$–$C_4$ alkoxy.

2. The compound according to claim 1, wherein

Q is oxygen or sulphur;

$R^1$ is hydrogen, cyano, fluorine, or chlorine;

$R^2$ is cyano;

$R^3$ is an optionally substituted methyl, ethyl, n- or i-propyl, n-, i-, s- or t-butyl, wherein the substituents are cyano-, fluorine-, chlorine-, methoxy-, or ethoxy-, $R^3$ is an optionally substituted cyclopropyl, cyclobutyl, cyclopentyl, or cyclohexyl, wherein the substituents are cyano-, fluorine-, chlorine-, bromine-, methyl-, ethyl-, n- or i-propyl-, $R^3$ is an optionally substituted phenyl, naphthyl, benzyl, phenylethyl, thienyl, pyrazolyl, pyridinyl, or quinolinyl, wherein the substituents are:
  fluorine, chlorine, bromine, cyano, nitro, carboxy, carbamoyl, thiocarbamoyl, methyl, ethyl, n- or i-propyl, trifluoromethyl, methoxy, ethoxy, n- or i-propoxy, difluoromethoxy, trifluoromethoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, dimethylaminosulphonyl, diethylaminosulphonyl, methoxycarbonyl, ethoxycarbonyl, n- or i-propoxycarbonyl;

$R^4$ is an optionally substituted cyclopentyl or cyclohexyl, wherein the substituents are cyano-, fluorine-, chlorine-, bromine-, methyl-, ethyl-, n- or i-propyl-, $R^4$ is an optionally substituted naphthyl, furyl, thienyl, oxazolyl, isoxazolyl, pyrazolyl, pyridinyl, or pyrimidinyl, wherein the substituents are:
  fluorine, chlorine, bromine, cyano, nitro, carboxy, carbamoyl, thiocarbamoyl, dimethylamino, dimethylaminosulphonyl, or diethylaminosulphonyl,
  optionally substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, wherein the substituents are fluorine- or chlorine-,
  optionally substituted methoxycarbonyl, ethoxycarbonyl, n- or i-propoxycarbonyl, wherein the substituents are fluorine-, chlorine-, bromine-, cyano-, methoxy-, or ethoxy-,
  optionally substituted phenyl, phenyloxy or phenylthio, wherein the substituents are fluorine-, chlorine-, bromine-, cyano-, methyl-, methoxy-, trifluoromethyl-, and/or trifluoromethoxy-;

$R^5$ is hydrogen, fluorine, chlorine, bromine or an optionally substituted methyl, ethyl, n- or i-propyl, wherein the substituents are fluorine- or chlorine-;

$R^6$ is an optionally substituted methyl, ethyl, n- or i-propyl, wherein the substituents are fluorine- or chlorine-; and $R^7$ is hydrogen, amino or an optionally substituted methyl, ethyl, n-or i-propyl, n-, i- or s-butyl, methoxy, ethoxy, n- or i-propoxy, n-, i- or s-butoxy, propenyl, butenyl, propinyl, or butinyl, wherein the substituents are fluorine or chlorine.

3. A method for controlling unwanted vegetation which comprises applying to such vegetation or to a locus from which it is desired to exclude such vegetation an herbicidally effective amount of the compound according to claim 1.

4. An herbicidal composition which comprises the compound according to claim 1 and an extender or surfactant.

* * * * *